(12) United States Patent
Jones-McMeans et al.

(10) Patent No.: US 9,737,646 B2
(45) Date of Patent: Aug. 22, 2017

(54) SMALL VESSEL STENT AND METHODS OF USE

(75) Inventors: Jennifer Jones-McMeans, Oakland, CA (US); Krishnankutty Sudhir, Santa Clara, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 774 days.

(21) Appl. No.: 13/429,268

(22) Filed: Mar. 23, 2012

(65) Prior Publication Data

US 2013/0046374 A1  Feb. 21, 2013

Related U.S. Application Data

(60) Provisional application No. 61/466,737, filed on Mar. 23, 2011.

(51) Int. Cl.
| | | |
|---|---|---|
| *A61F 2/04* | (2013.01) | |
| *A61F 2/82* | (2013.01) | |
| *A61L 31/16* | (2006.01) | |
| *A61F 2/86* | (2013.01) | |
| *A61L 31/02* | (2006.01) | |
| *A61L 31/10* | (2006.01) | |
| *A61F 2/915* | (2013.01) | |

(52) U.S. Cl.
CPC ............... *A61L 31/16* (2013.01); *A61F 2/04* (2013.01); *A61F 2/82* (2013.01); *A61F 2/86* (2013.01); *A61L 31/022* (2013.01); *A61L 31/10* (2013.01); *A61F 2/915* (2013.01); *A61L 2300/406* (2013.01); *A61L 2300/41* (2013.01); *A61L 2300/416* (2013.01); *A61L 2300/42* (2013.01); *A61L 2300/61* (2013.01)

(58) Field of Classification Search
USPC ................................................ 623/1.13, 1.42
See application file for complete search history.

(56) References Cited

PUBLICATIONS

Stone, Gregg W. et al.; Comparison of an Everolimus-Eluting Stent and a Paclitaxel-Eluting Stent in Patients With Coronary Artery Disease: A Randomized Trial; The Journal of the American Medical Association; Apr. 23/30, 2008—vol. 299, No. 16; pp. 1903-1913.*
The XIENCE™ V Everolimus Eluting Coronary Stent System: Instructions for Use; © 2008 Abbott Laboratories (Jun. 27, 2008); pp. 1-60.*

(Continued)

*Primary Examiner* — David Isabella
*Assistant Examiner* — Dinah Baria
(74) *Attorney, Agent, or Firm* — Randy Shen; Blakely, Sokoloff, Taylor & Zafman LLP

(57) ABSTRACT

A drug delivery device having an intraluminal stent for improving coronary luminal diameter of small vessels in patients with symptomatic heart disease is disclosed. The intraluminal stent includes struts having a thickness of less than approximately 110 μm. A polymer is adhered to the intraluminal stent that includes from about 50 μg/cm$^2$ to about 150 μg/cm$^2$ of everolimus therein. Quantitative coronary angiography measurements indicate that the drug delivery device provides an in-stent late loss of less than about 0.20 mm and an in-stent diameter stenosis of less than about 15% at 12 months following implantation in a human.

1 Claim, 2 Drawing Sheets

(56) References Cited

PUBLICATIONS

Moses JW et al., "Safety and Efficacy of the 2.25-mm Sirolimus-Eluting Bx Velocity Stent in the Treatment of Patients with De Novo Native Coronary Artery Lesions: the SIRIUS 2.25 Trial", American Journal of Cardiology, 2006; 98:1455-1460.*
Ardissino, D., et al. Sirolimus-eluting vs Unvoated Stents for Prevention of Restenosis in Small Coronary Arteries: a Randomized Trial. JAMA, 2004. 292:2727-34.
Doucet, S., et al. Stent Placement to Prevent Restenosis After Angioplasty in Small Coronary Arteries. Circulation 2001, 103(17):2029-33.
Meier, B., et al. Sirolimus-eluting Coronary Stents in Small Vessels. Am. Heart J., 2006. 151(5):1019.
Stone, G.W., et al. Comparison of an Everolimus-eluting Stent and a Paclitaxel-eluting Stent in Patients with Coronary Artery Disease: a Randomized Trial. JAMA, 2008. 299(16):1903-13.
Godino, C., et al. Clinical and Angiographic Follow-up of Small Vessel Lesions Treated with Paclitaxel-Eluting Stents (from the TRUE Registry). Am. J. Cardiol. 2008. 102(8):1002-8.

* cited by examiner

SMALL VESSEL STENT AND METHODS OF USE

CROSS-REFERENCE TO RELATED APPLICATION

This patent application claims priority to U.S. Provisional Patent Application Ser. No. 61/466,737, the disclosure of which is incorporated herein by reference.

FIELD OF THE DISCLOSED SUBJECT MATTER

The disclosed subject matter relates to a drug delivery device configured to treat small blood vessels and a method for the device's use. Particularly, the present disclosed subject matter is directed to an intraluminal stent for improving coronary luminal diameter of small vessels in patients having small vessels, such as diabetics, with symptomatic heart disease. The disclosed drug delivery device can also be used to treat patients with chron's disease.

BACKGROUND

A leading cause of mortality within the developed world is cardiovascular disease. Coronary disease is of most concern. Patients having such disease have narrowing in one or more coronary arteries. Generally, however, patients have narrowing in multiple coronary arteries. One treatment for the narrowing is stenting the blood vessel. Stenting involves the placement of a stent at the site of acute artery closure. This type of surgery has proved effective in restoring vessel patency and decreasing myocardial ischemia. However the exposure of currently used metallic stents to flowing blood can result in thrombus formation, smooth muscle cell proliferation and acute thrombotic occlusion of the stent.

Drug eluting stents ("DES") generally result in lower restenosis and revascularization rates as compared to bare metal stents in vessels having a diameter greater than approximately 3.0 mm ("large vessels"). See, e.g., Ardissino D, et al., Sirolimus-eluting vs uncoated stents for prevention of restenosis in small coronary arteries: a randomized trial, JAMA, 2004. 292: p. 2727-34; Doucet, S., et al., Stent placement to prevent restenosis after angioplasty in small coronary arteries, Circulation, 2001. 104(17): p. 2029-33; Meier, B., et al., Sirolimus-eluting coronary stents in small vessels, Am Heart J, 2006. 151(5): p. 1019 e1-7; Stone, G. W., et al., Comparison of an everolimus-eluting stent and a paclitaxel-eluting stent in patients with coronary artery disease: a randomized trial, JAMA, 2008. 299(16): p. 1903-13. However, vessels having a diameter of less than or less than 3.0 mm ("small vessels") continue to be clinically and angiographically at a disadvantage to larger vessels due to the inability of the small diameter to accommodate neointimal hyperplasia. See Godino, C., et al., Clinical and angiographic follow-up of small vessel lesions treated with paclitaxel-eluting stents (from the TRUE Registry), Am J Cardiol, 2008. 102(8): p. 1002-8. Various DES for treating small vessels having typical diameters of 2.25 mm, including the TAXUS® Atom, TAXUS® Liberte, Promus Element Stent, all three produced by Boston Scientific, Inc., the CYPHER®, produced by Johnson & Johnson, Inc. However, these small-vessel DES have not led to significantly reduced late loss diameter or percent diameter stenosis like their large-vessel DES counterparts. For example, for the core size Cypher used to treat vessels ≥2.5 mm to ≤3.5 mm, the 9 month in-stent late loss was 0.17 mm and 9 month in-stent restenosis rate was 3.2%. See Moses et al., "Sirolimus-eluting stents versus standard stents in patients with stenosis in a native coronary artery," N. Engl. J. Med. 2003, 348:1315-23; Cypher IFU, Cordis Corporation 2010. Whereas for the 2.25 mm Cypher 6 month restenosis rate was much greater at 11.7%. See Moses J W, et al., "Safety and efficacy of the 2.25-mm sirolimus-eluting Bx Velocity stent in the treatment of patients with de novo native coronary artery lesions: the SIRIUS 2.25 trial," American Journal of Cardiology 2006; 98(11):1455-1460. The core size Taxus Liberte used to treat vessels ≥2.5 mm to ≤4.0 mm had a 9 month in-stent late loss of 0.41 mm and in-stent restenosis rate of 11.38% and the 2.25 mm Taxus Liberte was associated with a higher restenosis rate of 13%. Even more dramatically the core size TAXUS Express stent, similar size to TAXUS Liberte, was associated with an in-stent restenosis rate of 8.64% at 9 months compared to a 9 month in-stent restenosis rate of 25.9%. See Stone G W et al., "Comparison of a polymer-based paclitaxel-eluting stent with a bare metal stent in patients with complex coronary artery disease: a randomized controlled trial," Journal of the American Medical Association 2005; 294(10):1215-1223.

Without being held to any theory, it is believed that the difficulty in treating small vessels with drug eluting stents is that the narrow lumen of the smaller diameter vessels are more prone to revascularization. Thus, the stents configured to treat such vessels do not achieve similar positive results, for example, as measured by in-stent late loss, as the larger counterparts. Accordingly, there remains a need in the art for small-vessel DES that produce improved angiographic and clinical outcomes in small vessels.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and devices particularly pointed out in the written description and claims thereof, as well as from the appended drawings.

To achieve these and other advantages and in accordance with the purpose of the disclosed subject matter, as embodied and broadly described, the disclosed subject matter relates to a device including a drug delivery device configured to treat a blood vessel having a diameter less than about 3 mm, and more particularly, greater than about 2.25 mm and less than about 2.5 mm. The drug delivery device includes an intraluminal stent, a polymer adhered to the intraluminal stent, and from about 50 $\mu g/cm^2$ to about 150 $\mu g/cm^2$ of everolimus applied to the intraluminal stent, wherein said drug delivery device provides an in-stent late loss at 8 months following implantation in a human of 0.20 mm or less, as measured by quantitative coronary angiography.

In one embodiment, the drug delivery device is implanted within a blood vessel having a diameter of less than about 3.0 mm. In another embodiment, the drug delivery device provides an in-stent % diameter stenosis at 8 months following implantation in a human of less than about 13%, as measured by quantitative coronary angiography. In another embodiment, the drug delivery device includes an intraluminal stent that comprises a body wherein at least a portion of said body is formed from an cobalt chromium alloy. In yet another embodiment, the drug delivery device comprises an intraluminal stent that has a diameter of between about 2.27 and 2.64 mm.

In yet another embodiment, the drug delivery device comprises an intraluminal stent body includes struts having a thickness of 88.8 µm. In still another embodiment, the strut thickness includes bare metal and polymer. In still another embodiment, the drug delivery device comprises an intraluminal stent and a polymer adhered to the intraluminal stent wherein everolimus is incorporated into the polymer at a dose of from about 100 µg/cm$^2$.

The disclosed subject matter also includes a method of inhibiting neointimal hyperplasia in a human artery comprising implanting in the lumen of an artery having a diameter of greater than about 2.25 mm and less than about 2.5 mm a drug delivery device comprising an intraluminal stent, a polymer adhered to the intraluminal stent, and from about 50 µg/cm$^2$ to about 150 µg/cm$^2$ of everolimus applied to the intraluminal stent, wherein said drug delivery device provides an in-stent late loss at 8 months following implantation in a human of 0.20 mm, as measured by quantitative coronary angiography. In one embodiment, the method provides an in-stent late loss in diameter at eight months following implantation of less than about 0.20 mm. In another embodiment, the method further provides an in-segment percent diameter stenosis at eight months following implantation of less than about twenty percent as measured by quantitative angiography. In another embodiment, the method further provides an in-stent percent diameter stenosis at eight months following implantation of less than about thirteen percent, as measured by quantitative coronary angiography. In yet another embodiment, the method further includes a drug delivery device wherein the everolimus is incorporated into the polymer at a dose of from about 100 µg/cm$^2$. In yet another embodiment, the method further includes a drug delivery device wherein the intraluminal stent as a diameter of between about 2.27 and 2.64 mm. In yet another embodiment, the method further includes a drug delivery device wherein the intraluminal stent comprises a body, wherein the body includes struts having a thickness of approximately 88.8 µm.

In another embodiment there is disclose a stent having a body with a deployed diameter of less than 3.0 mm. The deployed diameter may be approximately 2.25 mm. The body includes a plurality of struts having a thickness of less than approximately 95 µm. The strut thickness may be approximately 81 µm. The body is coated with a coating including at least one polymer adhered to the body wherein the coating has a thickness of less than approximately 12 µm. In some embodiments the coating thickness is between approximately 7.1 µm and 7.6 µm. A therapeutic agent is included in the polymer coating at a concentration of between about 50 µg/cm$^2$ and about 150 µg/cm$^2$. The therapeutic agent may be an immunosuppressive agent. In some embodiments the coating includes a first coating comprising a first polymer applied directly to the stent body and a second coating comprising a second polymer different from the first polymer applied to first coating. For example, the first coating may include PBMA, and, for example, the second coating may includes PVDF-HFP. In some embodiments, the therapeutic agent, e.g., everolimus, is included only within the second coating. The concentration may be about 100 µg/cm$^2$. Implantation of the stent in small vessels results an in-stent and in-segment late loss of less than about 0.20 mm and 0.16 mm, respectively, about eight months to about to about twelve months following implantation of the stent in the small vessel. Implantation of the stent in small vessels results an in-stent and in-segment late loss of less than about 0.20 mm±0.40 mm and 0.16 mm±0.41, respectively, about eight months to about to about twelve months following implantation of the stent in the small vessel. Additionally, the stent provides an in-stent and an in-segment diameter stenosis at approximately 8 months following implantation of less than about 15% and 22%, respectively, for example, the stent provide an in-stent and an in-segment diameter stenosis at approximately 8 months following implantation of 12.86%±19.58% and 20.85%±22.53%, respectively.

In accordance with the present subject matter there is also disclosed a method of treating a patient with a symptomatic heart disease. This method includes implanting a stent in a vessel of a patient. This stent may have a diameter of less than about 2.7 mm. The stent includes a body sized to fit within the blood vessel of the patient. The method also includes administering a therapeutic agent (e.g., everolimus, sirolimus, or paclitaxel) to the patient. The therapeutic agent may have a concentration of between about 50 µg/cm$^2$ and about 150 µg/cm$^2$. For example, in one embodiment, the therapeutic agent is everolimus at a concentration of about 100 µg/cm$^2$. The stent may be coated with a polymer. The therapeutic agent may be incorporated into the coating. The coating may have a thickness of between approximately 7.1 µm and 7.6 µm. The stent body may have a deployment diameter of approximately 2.25 mm. Eight to twelve months following implantation of the stent, there is an in-stent late loss of less than about 0.20 mm. There may also be an in-segment late loss of approximately 0.16 mm±0.41 mm. In some embodiments, the method includes administering antiplatelet therapy, such as aspirin, to the patient post implantation. The method may be used to treat multi-vessel bifurcation. One or more of the vessels may have a diameter of less than 2.5 mm. The method improves coronary luminal diameter in patients with symptomatic heart disease due to de novo native coronary artery lesions with a reference vessel diameter of 2.25 mm to less than about 2.5 mm.

In accordance with the present subject matter, and for use in a human population comprising at least two humans having an average target vessel diameter of between approximately 2.25 mm and 2.5 mm, there is disclosed a method for minimizing mean in-stent and mean in-segment late loss differences within the population to about 0.20 mm and about 0.16 mm, respectively. A stent is implanted into each human. The sent comprises a cobalt chromium alloy body having a deployed diameter of less than approximately 2.25 mm and struts having a strut thickness of less than approximately 81 µm, and a polymer coating comprising a first PBMA coating a second PVDF-HFP coating wherein everolimus is included in the second coating at a concentration of approximately 100 µg/cm2 and wherein the polymer coating has a thickness of approximately 7.5 µm. In each human, an in-stent MLD minuend and an in-segment MLD minuend is measured within about two-days after each implantation. Additionally, an in-stent MLD subtrahend and an in-segment MLD subtrahend is measured at about eight months after the implantation. Mean in-stent and mean in-segment late loss differences in the population are also determined.

There is also disclosed, in combination, a human vessel and a stent that slows the rate of neointimal hyperplasia in the vessel as evidenced by in-stent and in-segment late loss differences of about 0.20 mm and about 0.16 mm as determined at eight months following a percutaneous coronary intervention. The vessel has a diameter of between 2.0 mm and 2.3 mm. The stent comprises a cobalt chromium alloy body having a deployment diameter of less than approximately 2.3 mm and struts having a strut thickness of less than approximately 81 μm, and a polymer coating comprising a first PBMA coating a second PVDF-HFP coating wherein everolimus is included in the second coating at a concentration of approximately 100 μg/cm2 and wherein the polymer coating has a thickness of approximately 7.5 μm.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and device of the disclosed subject matter. Together with the description, the drawings serve to explain the principles of the disclosed subject matter.

DETAILED DESCRIPTION OF THE PREFERRED EMBODIMENT

Reference will now be made in detail to various embodiments of the disclosed subject matter, an example of which is illustrated in the accompanying drawings. The method and corresponding steps of the disclosed subject matter will be described in conjunction with the detailed description of the device.

The methods and devices presented herein are directed to a drug delivery device configured to treat a small blood vessel and a method for the device's use. Particularly, the methods and devices are directed to an intraluminal stent for improving coronary luminal diameter of small vessels in patients with symptomatic heart disease.

Figure 1:
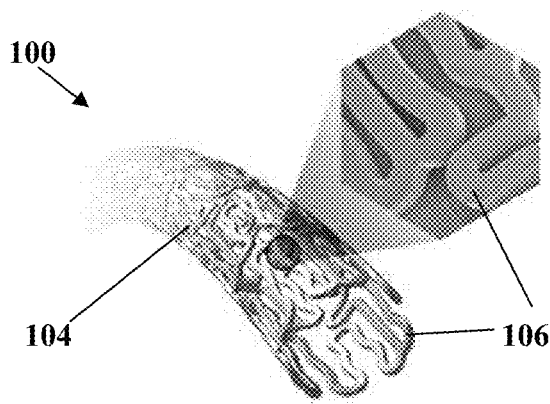
FIG. 1 is a schematic representation of the small vessel drug delivery device in accordance with the disclosed subject matter.

For purpose of explanation and illustration, and not limitation, a sample embodiment of a device in accordance with the disclosed subject matter is shown in FIG. 1 and is designated generally by reference character 100. The device 100 generally includes an intraluminal base stent, including a stent body 104, suitable for use in small vessels, i.e., vessels having a diameter of less than or equal to approximately 3.0 mm and an axial length of approximately 12 mm. Pre-deployment the stent is crimped on the balloon. The expanded diameter ranges from about 2.25 mm at lower balloon inflation pressures (e.g., about 8 atm) to about 2.59 mm at higher balloon inflation pressures (e.g., about 16 atm). In various embodiments, the base stent is designed for use in small vessels having diameters of greater than or equal to approximately 2.25 mm to 2.5 mm. The stent body 104 is preferably but not necessarily balloon expandable and may be fabricated from any suitable metallic material including, e.g., stainless steel, tantalum, nickel-titanium, cobalt-chromium, titanium, shape memory and superelastic alloys, and the nobel metals such as gold or platinum, as described in U.S. Pat. No. 6,939,373, which is herein incorporated by reference. In some embodiments the stent body is fabricated from L-605 cobalt chromium (CoCr) alloy. In other embodiments, the stent body 104 an be described more particularly as having a plurality of first peaks, second peaks, and valleys. Although the stent is not divided into separate elements, for ease of discussion references to peaks and valleys is appropriate. The number of peaks and valleys can vary in number for each ring depending upon the application. Thus, for example, if the stent is to be implanted in a coronary artery, a lesser number of peaks and valleys are required than if the stent is implanted in a peripheral artery, which has a larger diameter than a coronary artery.

The stent is used in patients who have narrowing in small coronary arteries that are greater than or equal to 2.25 mm to less than or equal to 2.50 mm in diameter and where the affected length of the artery is less than or equal to 28 mm long.

As shown in FIG. 1, stent body 104 is made up of a plurality of cylindrical rings which extend circumferentially around the stent when it is in a tubular form. The stent has a delivery catheter outer shaft diameter of 0.032" distally and 0.026" proximally. Each cylindrical ring has a cylindrical ring proximal end and a cylindrical ring distal end. Typically, since the stent is laser cut from a tube there are no discreet parts such as the described cylindrical rings and links However, it is beneficial for identification and reference to various parts to refer to the cylindrical rings and links and other parts of the stent as follows.

Each cylindrical ring defines a cylindrical plane which is a plane defined by the proximal and distal ends of the ring and the circumferential extent as the cylindrical ring travels around the cylinder. Each cylindrical ring includes cylindrical outer wall surface which defines the outermost surface of the stent, and cylindrical inner wall surface which defines the innermost surface of the stent. Cylindrical plane follows the cylindrical outer wall surface.

In keeping with the invention, undulating link is positioned within cylindrical plane. The undulating links connect one cylindrical ring to an adjacent cylindrical ring and contribute to the overall longitudinal flexibility to the stent due to their unique construction. The flexibility of the undulating links derives in part from curved portion connected to straight portions wherein the straight portions are substantially perpendicular to the longitudinal axis of the stent. Thus, as the stent is being delivered through a tortuous vessel, such as a coronary artery, the curved portions and straight portions of the undulating links will permit the stent to flex in the longitudinal direction which substantially enhances delivery of the stent to the target site. The number of bends and straight portions in a link can be increased or decreased from that shown, to achieve differing flexibility constructions. With the straight portions being substantially perpendicular to the stent longitudinal axis, the undulating link acts much like a hinge at the curved portion to provide flexibility. A straight link that is parallel to the stent axis typically is not flexible and does not add to the flexibility of the stent.

The stent body 104 can be described more particularly as having a plurality of peaks and valleys. Although the stent is not divided into separate elements, for ease of discussion references to peaks and valleys is appropriate. In keeping with the invention, each of the cylindrical rings has a plurality of peaks which have struts attached to an apex. The struts can be either curved or straight depending upon the particular application.

The stent body 104 of the present invention can be made in many ways. One method of making the stent is to cut a thin-walled tubular member, and to remove portions of the tubing in the desired pattern for the stent, leaving. In accordance with the invention, the tubing is cut in the desired pattern by means of a machine-controlled laser as is well known in the art. In keeping with the invention, the struts have a thickness of less than approximately 110 µm. In a specific embodiment, the struts have a thickness of 81 µm.

The base stent is coated with active and inactive ingredients. The inactive ingredients include polymers, e.g., poly (N-acetylglucosamine) (Chitin), Chitosan, poly(3-hydroxyvalerate), poly(D,L-lactide-co-glycolide), poly(1-lactide-co-glycolide) poly(3-hydroxybutyrate), poly(4-hydroxybutyrate), poly(3-hydroxybutyrate-co-3-hydroxyvalerate), polyorthoester, polyanhydride, poly (glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly (glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), poly(vinylidene fluoride), poly(vinylidene fluoride-co-hexafluoropropylene), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, fullerenes and lipids. In a specific embodiment, the inactive ingredients re the polymers poly n-butyl methacrylate (PBMA) and PVDF-HFP, which is comprised of vinylidene fluoride and hexafluoropropylene monomers. PVDF-HFP is a non-erodible semi-crystalline random copolymer with a molecular weight of 254,000 to 293,000 daltons. PBMA is a homopolymer with a molecular weight of 264,000 to 376,000 daltons.

The active ingredient is a therapeutic agent that can include any substance capable of exerting a therapeutic or prophylactic effect. Examples of therapeutic agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin I1, actinomycin X1, and actinomycin C1. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin.

In a specific embodiment the active agent is everolimus. Everolimus, developed by Novartis Pharma AG, is a proliferation signal inhibitor, or mTOR inhibitor. It is a semi-synthetic macrolide immunosuppressant, synthesized by chemical modification of rapamycin (sirolimus). Everolimus has been shown to inhibit in-stent neointimal growth in coronary vessels following stent implantation due to its anti-proliferative properties.

In one embodiment, PBMA, which adheres well with metallic materials and other polymers, is used as a primer to coat the base stent. PVDF-HFP is used as a drug matrix that is mixed with everolimus. The PVDF-HFP/everolimus mixture is adhered to the surface of the PBMA coated stent. In a specific embodiment, this PVDF-HFP/everolimus mixture comprises 83% polymer and 17% everolimus. The thickness of the polymer coating is less than approximately 10 µm. In a specific embodiment, the thickness of the polymer coating is 7.1 µm. The concentration of the everolimus in the copolymer is about 50 µg/cm$^2$ to about 150 µg/cm$^2$. In a specific embodiment the concentration of the everolimus in the copolymer is 100 µg/cm$^2$. Systems and methods for coating stents are disclosed in U.S. Pat. No. 8,003,157, which is herein incorporated by reference.

The design attributes described above are understood to provide sufficient healing and endothelial coverage of the stent struts to contribute to reduced neointimal hyperplasia and reduced restenosis risk. The stent may be implanted according to the following steps. The vascular site should be prepared according to standard practice. The lesion should be Pre-dilated with a PTCA catheter of appropriate length and diameter for the vessel/lesion to be treated. The longitudinal length of pre-dilatation by the PTCA balloon should be limited to avoid creating a region of vessel injury that is outside the boundaries of the stent. Neutral pressure should be maintained on the inflation device attached to the delivery system. The rotating hemostatic valve should be open as wide as possible. The delivery system should be backloaded onto the proximal portion of the guide wire while maintaining guide wire position across the target lesion. The delivery system should be advanced into the guiding catheter and over the guide wire to the target lesion. When using a Rapid Exchange (RX) system the hypotube should be kept straight. Guiding catheter stability should be ensured before advancing the stent system into the coronary artery. Next, the delivery system is advanced over the guide wire to the target lesion under direct fluoroscopic visualization. Radiopaque balloon markers may be used to position the stent across the lesion. Angiography may be used to confirm stent position. If the position of the stent is not optimal, it should be carefully repositioned or removed The balloon markers indicate both the stent edges and the balloon shoulders. Expansion of the stent should not be undertaken if the stent is not properly positioned in the target lesion. Then, the rotating hemostatic valve should be tightened.

Next, the stent may be deployed. The stent should be deployed slowly by pressurizing the delivery system in 2 atm increments, every 5 seconds, until completely expanded. Accepted practice generally targets an initial deployment pressure that would achieve a stent inner diameter ratio of about 1.1 times the reference vessel diameter. Pressure should be maintained for 30 seconds. If necessary, the delivery system can be repressurized or further pressurized to assure complete apposition of the stent to the artery wall. The entire lesion and balloon treated area (including dissections) should be covered with the stent, allowing for adequate stent coverage into healthy tissue proximal and distal to the lesion. The balloon should be deflated by pulling negative on the inflation device for 30 seconds.

Post procedure, when crossing a newly a newly deployed stent with an intravascular ultrasound (IVUS) catheter, a coronary guide wire, a balloon catheter or delivery system, care should be exercised to avoid disrupting the stent placement, apposition, geometry, and/or coating. Additionally, it may be desirable to provide antiplatelet therapy post-procedure. Patients who require early discontinuation of antiplatelet therapy (e.g., secondary to active bleeding) should be monitored carefully for cardiac events. At the discretion of the patient's treating physician antiplatelet therapy should be restarted as soon as possible.

A typical angiographic parameter for measuring stent performance is called "late-lumen loss" or simply "late loss." It is calculated by subtracting the follow-up minimum lumen diameter ("MLD") from the post-procedural MLD (i.e., late loss=post-procedural MLD–follow-up MLD). This measurement is considered a good estimator of in-stent neointimal hyperplasia. Accordingly, it is frequently used in clinical studies as a surrogate endpoint for clinical efficacy of coronary devices. The term "in-stent late loss" refers to a late loss calculation made from MLD measurements taken within a stent's boundaries. The tem "in-segment" late loss refers to a late loss calculation made from MLD measurements taken within the diseased portion of the vessel where the stent is placed. In some instances, the in-segment portion extends approximately 5 mm from either edge of the stent margins such that the in-segment length is approximately 10 mm longer than the in-segment length. Accordingly, in-segment calculations include MLD measurements outside the stent margins.

Another angiographic parameter for measuring stent performance is called "percent diameter stenosis," or simply "diameter stenosis." It is calculated by dividing late loss by the post-procedural MLD and multiplying by 100, (i.e., percent diameter stenosis=(late loss/post-procedural MLD)*100)). As with late loss, the modifying terms "in-stent" and "in-segment" refer to the locations over which MLD measurements used in the calculation may be taken.

Reduced neointimal hyperplasia is associated with low in-stent and in-segment late loss measurements and low rates of in-stent and in-segment diameter stenosis and angiographic binary restenosis. Such results are beneficial for smaller diameter vessels that are less able to accommodate neointimal growth than larger vessels.

Evidence that the present invention exerts an effect on remodeling comes from human implant studies that were undertaken to ensure that the invention would work for its intended purpose, i.e., to reduce neointimal hyperplasia within small vessels as measured by in-stent late loss and in-stent diameter stenosis. Specifically, a prospective, single-arm, open-label study was conducted at 33 centers in United States. Consecutive patients with a maximum of two de novo native coronary artery lesions ≤28 mm in length and in vessels ≥2.25 mm to <2.5 mm in diameter were enrolled. Of the 150 subjects enrolled, 144 subjects received at least one drug delivery device in accordance with the above described embodiments. Specifically, these patients each received one drug delivery device comprising a CoCr base stent having approximately a 2.25 mm diameter and approximately a 12 mm length, with a stent body having struts with a thickness of approximately of 81 μm. The base stent coating comprised PBMA and PVDF-HFP combined with everolimus. The thickness of this coating was approximately 7.6 μm and the concentration of evorlimus was approximately 100 μg/cm$^2$. The mean age was 62.97 years±10.59 years. 61.8% (89/144) of the population was male and 39.2% (56/143) were diabetic. The majority of target lesion treatment occurred in the left anterior descending (LAD) coronary artery at 40.7% (59/145), followed by 31.0% (45/145) in the circumflex (LCX)/ramus, and 28.3% (41/145) located in the right coronary artery (RCA). Target lesion location was further categorized by target coronary artery surgery study (CASS) segment location, in which target lesions were mainly located in side-branches at 31.7% and major side-branches at 31.0%. The mean reference vessel diameter ("RVD") was 2.13 mm±0.23 mm and the mean lesion length was 13.38 mm±5.31 mm. 72.2% (104/144) of subjects had one vessel treated and 27.8% (40/144) had two vessels treated.

The data revealed a 1-year target lesion failure ("TLF") rate of 8.1% (11/136) in which the upper limit of the one-sided 95% confidence interval was 13.0% and therefore met the performance goal of 20.4% (p<0.0001). The 1 year cardiac death rate was 1.5% (2/136), the target vessel myocardial infarction rate was 1.5% (2/136) and clinically indicated target lesion revascularization rate was 5.1%

(7/136). The 393 day academic research consortium defined definite/probable stent thrombosis rate was 1.5% (2/136).

Figure 2:
FIG. 2 is a chart indicating the late loss effectiveness of the small vessel drug delivery device.
Figure 3:
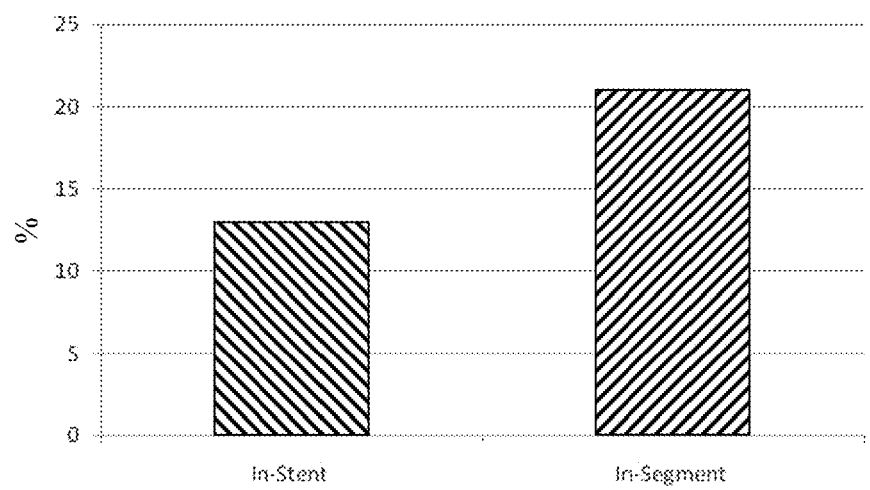
FIG. 3 is a chart indicating diameter stenosis effectiveness of the small vessel drug delivery device.
Figure 4:
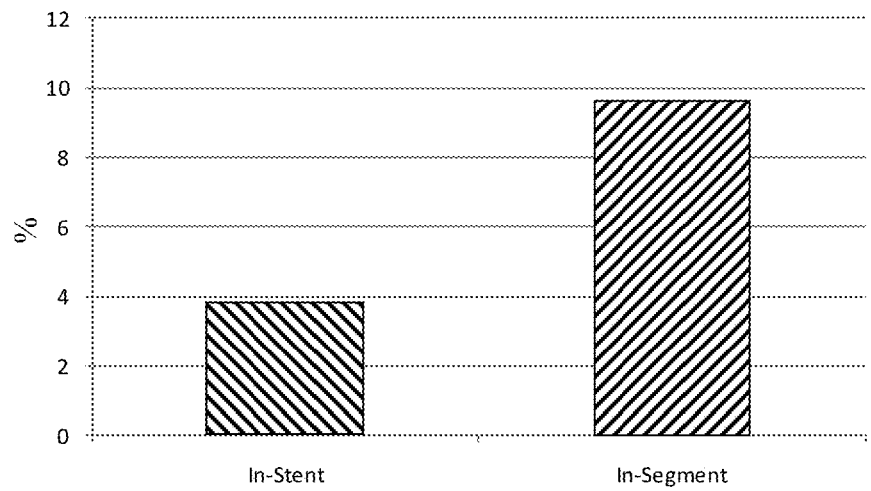
FIG. 4 is a chart indicating binary restenosis rates of the small vessel drug delivery device.

Sixty-nine subjects were included in a 240 day quantitative coronary angiographic cohort, and data were produced for 52 of these patients. Referring to FIG. 2, the 240 day (±28 days) angiographic data revealed a 0.16 mm±0.41 mm in-segment and 0.2 mm±0.4 mm in-stent late loss. Referring to FIG. 3, the angiographic data revealed a 20.85%±22.53% in-segment and 12.86%±19.58% in-stent diameter stenosis. Referring to FIG. 4, the in-segment and in-stent binary restenosis rates were 9.6% (5/52) and 3.8% (2/52), respectively.

Commercially available small-vessel DES have greater strut thicknesses and polymer thicknesses compared to the DES of the present invention. For example, the 2.25 mm TAXUS® Express is associated with a strut thickness of 246 µm and polymer thickness of 16 µm, the 2.25 mm TAXUS® Liberte is associated with a strut thickness of 97 µm and a polymer thickness of 16 µm, and the 2.25 mm Cypher® DES is associated with a strut thickness of 140 µm and a polymer thickness of 12.6 µm. The lower strut thickness and polymer thickness of the present invention compared to the other 2.25 mm DES are understood by the inventors to be associated with the more favorable angiographic and clinical results (e.g., lower revascularization rates).

Table 1 provides a functional comparison between the drug delivery device of the present invention and commercially available 2.25 mm DES. It is apparent from this comparison that the drug delivery device of the present invention provides beneficial angiographic and clinical outcomes over the commercially available small-vessel DES.

TABLE 1

Comparison of 2.25 mm Drug Eluting Stents

|  | Present Invention (n = 150) | 2.25 mm Cypher[1-2] (n = 100) | 2.25 mm Taxus Liberte[3-4] (n = 261) | 2.25 mm Taxus Express Atom (n = 108)[5] |
|---|---|---|---|---|
| Angiographic outcomes | | | | |
| Strut + Polymer Thickness (µm) | 88.6 | 152.6 | 113 | 262 |
| RVD | 2.13 ± 0.23 | 2.04 ± 0.29 | 2.02 ± 0.30 | 2.07 ± 0.31 |
| Lesion Length | 13.38 ± 5.31 | 12.1 ± 7.0 | 14.5 ± 6.9 | 16.6 ± 9.7 |
| In-stent LL (mm) | 0.20 ± 0.40 | 0.36 ± 0.50 | — | 0.49 ± 0.61 |
| In-segment LL (mm) | 0.16 ± 0.41 | 0.23 ± 0.43 | 0.16 ± 0.40 | 0.36 ± 0.53 |
| In-stent % DS | 12.86 ± 19.58 | 18.48 ± 26.66 | — | — |
| In-segment % DS | 20.85 ± 22.53 | 33.81 ± 19.95 | 31.7 ± 18.2 | — |
| In-stent ABR % | 3.8 | 11.7 | — | 24.7 |
| In-segment ABR % | 9.6 | 16.9 | 17.9 | 31.2 |
| Clinical outcomes | | | | |
| Death % | 1.5 | 2.1 | 1.2 | 1.9 |
| MI % | 1.5 | 4.3 | 2.4 | 5.7 |
| TLR % | 5.1 | 7.3 | 6.1 | 10.4 |
| Stent Thrombosis (n) | 2 | 2 | 1 | 1 |
| MACE % | 8.1 | 11.5 | 13.4 | 18.9 |
| TVF % | 11 | 14.6 | — | — |

Present invention 8 month angiographic follow-up; 2.25 mm TAXUS Liberte 9 month follow-up, 2.25 mm TAXUS Atom 9 month follow-up and 2.25 mm Cypher 6 month follow-up
Stent thrombosis was defined per ARC for the SPIRIT Small Vessel trial and the Taxus Atlas trial. Per protocol definition for 2.25 mm Cypher and 2.25 mm TAXUS Atom
Major Adverse Cardiac Events ("MACE") rate and TLF rate were the same in the SPIRIT Small Vessel trial
9 month data presented
Cypher uses all death instead of cardiac death
In TAXUS Atlas the MACE definition was the same of the SPIRIT Small Vessel Target Vessel Failure ("TVF") definition
Stent thrombosis: ARC definition used for Taxus Liberte and the present invention. Per protocol definitions used for Cypher and Taxus Express Atom.
MACE definitions differ across all trials
[1]Instructions For Use Cypher ® Sirolimus-eluting Coronary Stent on RAPTOR ™ Over-the-Wire Delivery System and Cypher ® Sirolimus-eluting Coronary Stent on RAPTORRAIL ™ Rapid Exchange Delivery System Cordis ® 2009.
[2]Moses JW, Nikolsky E, Mehran R, et al. Safety and efficacy of the 2.25-mm sirolimus-eluting Bx Velocity stent in the treatment of patients with de novo native coronary artery lesions: the SIRIUS 2.25 trial. The American journal of cardiology 2006; 98: 1455-60.
[3]Turco MA. TAXUS ATLAS Small Vessel and Long Lesion: First Report of Nine-Month Clinical and Angiographic Results. TCT 2007.
[4]Turco MA, Ormiston JA, Popma JJ, et al. Reduced risk of restenosis in small vessels and reduced risk of myocardial infarction in long lesions with the new thin-strut TAXUS Liberte stent Journal of the American College of Cardiology 2008; 1: 699-709.
[5]Stone GW, Ellis SG, Cannon L, et al. Comparison of a polymer-based paclitaxel-eluting stent with a bare metal stent in patients with complex coronary artery disease: a randomized controlled trial. JAMA 2005; 294: 1215-23.

The methods and devices presented herein also may be directed to a drug delivery device configured to treat gastrointestinal disorders including inflammatory bowel disease, and a method for the device's use. Particularly, the methods and devices are directed to an a stent for treating malignant obstructions and preventing intestinal stenosis.

One type of inflammatory bowel disease for which the present subject matter is particularly suited is Crohn's disease. Crohn's disease is an autoimmune disorder that causes effected individuals to have chronic inflammation in the gastrointestinal tract. The disease generally involves the small intestine and/or large intestine, whereby the inflammation causes a thickening of the intestinal wall. In some instances, Crohn's disease also causes inflammation of the rectum and mouth. The small intestine is the part of the gastrointestinal tract following the stomach and followed by the large intestine, and is where much of the digestion and absorption of food takes place. The large intestine is the third-to-last part of the digestive system in vertebrate animals. Its function is to absorb water from the remaining indigestible food matter, and then to pass useless waste material from the body. The rectum is the final straight portion of the large intestine.

Symptoms of Crohn's disease may include abdominal cramps, fever, fatigue, loss of appetite, tenesmus, diarrhea, weight loss, constipation, eye inflammation, fistulas near the rectum, joint pain and swelling, mouth ulcers, rectal bleeding, bloody stools, skin lumps, and swollen gums. Crohn's disease is typically treated by the administration of various drugs, e.g., orally, rectally, or by injection. Such drugs generally include anti-inflammatory drugs (e.g., sulfasalazine, mesalamine, corticosteroids, and budesonide) to reduce inflammation commonly associated with Crohn's disease, an/or immune system suppressors (e.g., azathioprine, mercaptopurine, infliximab, adalimumab, certolizumab pegol, methotrexate, cyclosporine, and natalizumab). Immune system suppressors suppress immune system response, which prevents inflammation indirectly. Antibiotics (e.g., Metronidazole and Ciproflaxacin) are also used. These antibiotics reduce the amount of drainage and sometimes heal fistulas and abscesses in people with Crohn's disease. Antibiotics may also help reduce harmful intestinal bacteria and suppress the intestine's immune system, which can trigger symptoms. Other categories of medications that are prescribed to individuals having Crohn's disease include: anti-diarrheals, laxatives, pain relievers, iron supplements, vitamin b-12, calcium, and vitamin D.

In accordance with one aspect of the disclosed subject matter, a drug eluting stent is provided for the treatment of Crohn's disease. In one embodiment, the stent includes a drug disposed on or within a polymer-coated stent. Dosage concentrations of the drug included on the stent, within the polymeric coating, may range from about 0.1 $\mu g/c^{m2}$ to 500 $\mu g/c^{m2}$, depending on the type of active agent used and whether the stent is intended for use in babies, children, or adults. For example, the stent can be configured for pediatric indications.

In one embodiment, the stent includes a stent body comprising For example, the structural features may include first peaks, second peaks, and valleys as shown in FIG. 1. The stent body may also include a truss structure. The structural features may be curved, straight, or both. The stent body may also be designed such that the stiffness and/or resiliency of the stent, both before and after expansion, is dependent on the structural features. For example, the resiliency of a stent indicated for use in the rectum would need to be different than the resiliency of a stent for use in the intestine at least due to the muscular processes and motions during a bowel movement. Accordingly, in some embodiments, the structural features may have varying thicknesses to effect a varying resiliency to the stent body. Such features would be useful for rectal use of the stent because when the rectum becomes full, the increase in intrarectal pressure forces the walls of the anal canal apart, allowing the fecal matter to enter the canal. The rectum shortens as material is forced into the anal canal and peristaltic waves propel the feces out of the rectum. The internal and external sphincter allow the feces to be passed by muscles pulling the anus up over the exiting feces.

In some embodiments, the stent may be placed in either the small intestine, the large intestine, or the rectum. The average length of the small intestine in an adult human male is 22 feet 6 inches (6.9 m), and in the adult female 23 feet 4 inches (7.1 m). However, it can vary greatly, from as short as 15 feet (4.6 m) to as long as 32 feet (9.8 m). The average diameter of the adult small intestine is approximately 2.5-3 cm. On average, the large intestine in humans is typically four to five times shorter than the small intestine—about 1.5 meters long. On average, the diameter of the large intestine of an adult human measures about 7.6 centimeters in diameter. The rectum is similar in diameter to the large intestine, and is about 12 cm in length. In babies, the small intestine may be, on average, as short as about 200 cm in length, having a diameter, on average, as small as about 1.0 cm in diameter. In children, the intestinal dimensions range between a baby's average dimensions and an adult's average dimensions. Based on these dimensions, various sizes of stents for treatment of intestinal diseases are needed to treat adults, children, and babies. Accordingly, the expanded diameter of stents adapted for use in adults, children, and babies are preferably chosen to range from a smaller small-intestine baby size to a larger large-intestine adult size. Accordingly, the diameters of such stents are designed to be approximately 0.5 cm to 15 cm, sized in various increments. Sample increments may be 0.1 cm, 0.25 cm, 0.5 cm, 0.75 cm, 1 cm, or 2 cm. Additionally various lengths of stents may be designed to maintain an opening at a point of a stricture. Sample lengths include, 1 cm, 2, cm, 3 cm, 5 cm, 8 cm, 10 cm, 20 cm, 30 cm, 50 cm, and 100 cm.

In some embodiments, the stent may also be made entirely from a polymeric material such as those listed above. The polymeric material may be bioabsorbable. The polymeric material may also include an active agent such as those listed above. In some embodiments, the stent may be designed to absorb over predefined periods of time, e.g., approximately one month, approximately six months, approximately one year, approximately two years, approximately five years, or approximately ten years. Because some patients may experience negative reactions to a stent in the intestine or rectum at different durations from the point in time when the stent is delivered, these patients can be treated with stents that degrade over a shorter period of time than the time over which the negative reaction occurs. For example, some patients may experience complications at approximately one year after stent delivery. Accordingly, such patients could be treated with a stent lasting, e.g., 8 months. Then, when the stricture begins to return, a new stent may be delivered to the site.

The stent may be inserted, e.g., endoscopically by a surgeon using, e.g., fluoroscopic guidance and conscious sedation, into the rectum, small intestine, or large intestine. An endoscope may be passed to the site of lesion. The stricture (i.e., location of stenosis) may be assessed fluoroscopically by injection of, e.g., a water soluble contrast through an endoscopic retrograde cholangiopancreatography catheter. A guidewire is used to cross the stricture. A stent is passed over the guidewire through the biopsy channel of the colonoscope. Finally, the stent is deployed under direct endocscopic and fluoroscopic guidance. An x-ray may be taken to confirm stent expansion and position. Once positioned, the agents and/or drugs contained in the polymer are released from the polymer to provide a therapeutic effect to the diseased tissue. In some embodiments, the stent and the agents and/or drugs will heal, prevent, or retard ailments of the intestine and rectum, such as strictures.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and device of the disclosed subject matter without departing from the spirit or scope of the disclosed subject matter. Thus, it is intended that the disclosed subject matter include modifications and variations that are within the scope of the appended claims and their equivalents.

What is claimed is:

1. A stent comprising:
  a body having a deployed diameter of 2.25 mm, the body including a plurality of struts having a thickness of less than approximately 95 µm;
  a coating including at least one polymer adhered to the body wherein the coating has a thickness between approximately 7.1 µm and 7.6 µm; and
  a therapeutic agent included in the polymer coating at a concentration about 100 µg/cm$^2$,
  wherein 8 months to about 12 months following implantation of the stent in the small vessel results an in-stent and in-segment late loss of less than about 0.20 mm and 0.16 mm, respectively, and in-segment and in-stent binary restenosis rates of about 9.6% and 3.8%, respectively.

* * * * *